United States Patent [19]

Akiyama et al.

[11] 3,976,688

[45] Aug. 24, 1976

[54] PROCESS FOR PREPARING UNSATURATED CARBOXYLIC ACIDS

[75] Inventors: Shinichi Akiyama; Haruhisa Yamamoto, both of Takaoka, Japan

[73] Assignee: Nippon Zeon Co., Ltd., Tokyo, Japan

[22] Filed: Nov. 14, 1974

[21] Appl. No.: 523,683

[30] Foreign Application Priority Data

Nov. 26, 1973  Japan.............................. 48-132432
Nov. 26, 1973  Japan.............................. 48-132433

[52] U.S. Cl............................. 260/530 N; 252/432; 252/435; 252/437
[51] Int. Cl.²......................................... C07C 51/32
[58] Field of Search....................... 260/530 N, 413; 252/435, 437, 432

[56] References Cited
UNITED STATES PATENTS 3,795,703   3/1974   Niina .............................. 260/530 N
3,865,873   2/1975   Oda .................................. 260/530N
3,875,220   4/1975   White ............................... 260/530N

*Primary Examiner*—Vivian Garner
*Attorney, Agent, or Firm*—Sherman & Shalloway

[57] ABSTRACT

A process for the preparation of an unsaturated carboxylic acid which comprises reacting an unsaturated aldehyde with molecular oxygen in the vapor phase in the presence of an oxidation catalyst composition having the following empirical formula $$Mo_a P_b L_c T_d O_e$$

wherein L is at least one element selected from the group consisting of Rb, Cs and K; T is at least one element selected from the group consisting of Ba, Cd, W, Bi, Nb, B, Pb and Pd; and $a$, $b$, $c$, $d$, and $e$ each represent the number of atoms of each element; the atomic ratio of $a:b:c:d$ is 12:0.1–8:0.1–8:0.1–8 and $e$ is the number of oxygen atoms determined by the valence requirement of the other elements present.

16 Claims, No Drawings

PROCESS FOR PREPARING UNSATURATED CARBOXYLIC ACIDS

This invention relates to a process for preparing unsaturated carboxylic acids by the vapor phase oxidation of unsaturated aldehydes using a specific catalyst which can give the unsaturated carboxylic acids in high selectivity and yield and has a long active lifetime.

Prior patents and literature relating to the vapor phase catalytic oxidation of unsaturated aldehydes are directed chiefly to the production of acrylic acid from acrolein, and very few relate to the production of methacrylic acid from methacrolein. Actually, many of the catalysts which give good results in the oxidation of acrolein exhibit low activity (low conversion) when applied to the oxidation of methacrolein. If the reaction is carried out at an elevated temperature in order to increase the conversion of methacrolein, side reactions such as a complete oxidation reaction (the formation of $CO$ and $CO_2$) occur to reduce the yield (per pass) and selectivity of methacrylic acid. On the other hand, the catalysts so far suggested for the oxidation of methacrolein are commercially unsuitable and not entirely satisfactory for one or combinations of the following reasons, such as low activity, short active life and low productivity (space time yield for methacrylic acid) because of the necessity to prolong the reaction time or to reduce the methacrolein concentration in the feed gas.

Under such circumstances, it has been considered very difficult to produce methacrylic acid commercially by the oxidation of methacrolein, in spite of the fact that the production of acrylic acid from acrolein has been carried out commercially. Accordingly, it has been concluded that the development of catalysts useful for the oxidation of methacrolein must be studied with different considerations than the catalysts used for the oxidation of acrolein.

Accordingly, it is an object of this invention to provide a new catalyst which can be used as an oxidation catalyst and which eliminates the defects of conventional oxidation catalysts for methacrolein, and which has excellent catalytic activity (namely, giving high yield, selectivity and productivity of methacrylic acid) and a long active lifetime.

Another object of this invention is to provide a new catalyst which is effective not only for oxidation of methacrolein but also for oxidation of other unsaturated aldehydes such as acrolein.

These objects of the present invention can be achieved by using an oxidation catalyst composition comprising a catalytic oxide of molybdenum, phosphorus, at least one element selected from the group consisting of rubidium, cesium and potassium, and at least one element selected from the group consisting of barium, cadmium, tungsten, bismuth, niobium, boron, lead and palladium, the catalyst composition having the following empirical formula

wherein L is at least one element selected from the group consisting of Rb, Cs and K; T is at least one element selected from the group consisting of Ba, Cd, W, Bi, Nb, B, Pb and Pd; and $a$, $b$, $c$, $d$ and $e$ each represent the number of atoms of each element; the preferred atomic ratio of $a:b:c:d$ is in the range of about $12:0.1-8:0.1-8:0.1-8$; and e is the number of oxygen atoms determined by the valence requirements of the other elements present; a more preferred atomic ratio of $a:b:c:d$ is in the range of about $12:0.3-5:0.3-5:0.3-5$.

The catalysts according to the present invention can be used as an oxidation catalyst to produce unsaturated carboxylic acids in higher yields and selectivities than conventional catalysts used in the stable oxidation reaction of unsaturated aldehydes under feasible reaction conditions. Furthermore, the problem of the active lifetime of the catalyst has now been solved by the new catalyst used in this invention. Since the catalytic life can be maintained at a high level for prolonged periods of time, the reaction can be performed continuously over an extended period of time.

The catalyst may be made, for example, by the oxide mixing method, the evaporative drying method or the coprecipitation method, all of which are well known in the art. The starting constituent elements of the catalyst do not always have to be in the form of an oxide but may be in the form of a metal, metal salt, acid or base so long as they can be converted to the corresponding metal oxides by calcination. Typical examples include salts such as ammonium salts, nitrate or halides; free acids such as molybdic acid or phosphoric acid; heteropolyacids containing molybdenum such as phosphomolybdic acid, and heteropolyacid salts such as ammonium salt of the phosphomolybdic acid.

The catalyst can be prepared, for example, by mixing an aqueous solution containing a water-soluble compound of the T element with an aqueous solution containing ammonium molybdate, adding on aqueous solution containing phosphoric acid and an aqueous solution containing a nitrate of the L element such as cesium nitrate, evaporatively drying the mixture while stirring, calcining the solid obtained, pulverizing the calcined product, and then, if necessary, molding it into pellets. Other examples of the catalyst preparation are described for example, in the working examples to be given later. Preferably, the catalyst is prepared by mixing the starting compounds so that the constituent elements will form complex compounds such as heteropolyacids, their acid salts or ammonium salts, calcining the obtained complex compounds to produce the corresponding oxides in situ, pulverizing the calcined product and then, if necessary, molding it into pellets. Those skilled in the art can select the desired method of preparing the catalyst. It is not yet clear however, in what state the individual elements of the catalyst composition, including oxygen, are in during the reaction when the catalyst is exhibiting its catalytic action.

While the catalyst can be used in the molded or powdered form, it is also possible to use it after dilution with an inert diluent. If desired, the catalyst can be deposited on a suitable inert carrier material. Examples of suitable carriers include alumina, silicon carbide, graphite, inert titania, zirconium oxide, thorium chloride, pumice, silica gel, or celite. The amount of the diluent or carrier is not critical since it has no substantial effect on the activity of the catalyst.

When the catalysts of the present invention are used to prepare an unsaturated carboxylic acid by reacting an unsaturated aldehyde with molecular oxygen at an elevated temperature in the vapor phase, the unsaturated aldehyde may preferably be acrolein or methacrolein. The source of molecular oxygen can be pure oxygen or air. Furthermore, it is possible to introduce into the reaction zone an inert diluent gas such as steam, nitrogen, argon, carbon dioxide, helium or a saturated hydrocarbon, for example, methane, ethane, propane or pentane.

The concentration of the unsaturated aldehyde in the feed gas to be introduced into the reactor is preferably from about 1 to about 25% by volume. On the other hand, the molar ratio of the starting unsaturated aldehyde to molecular oxygen is conveniently about 1:(0.1-25.0), preferably about 1:(0.1-20.0). The reaction temperature is usually in the range of about 300° to 500°C., preferably about 330° to about 450°C., and the reaction pressure can be from a reduced pressure of less than atmospheric pressure to a superatmospheric pressure up to about 15 atms. Preferably, the reaction pressure is about 0.5 to about 10 atmospheres. The contact time (on the basis of 0°C. and 1 atm.) is from about 0.1 to about 20 seconds, preferably about 0.1 to about 15 seconds. These conditions are suitably determined relative to each other according to the catalyst employed and the reaction conditions. The type of reactor with which the catalysts of the present invention is used may be any of those which are conventional, such as the fluidized, moving or fixed bed type. The reaction product can be recovered by known techniques; for example, condensation and liquefaction by means of a condenser or the extraction with water or a suitable solvent.

The invention is illustrated by the following Examples. The conversion of the unsaturated aldehyde, the yield of the unsaturated carboxylic acid and the selectivity therefor are defined below. The analysis was carried out by gas chromatography in all cases.

cined at 450°C. for 16 hours in a muffle furnace, pulverized and screened to a screen size of 4 to 8 mesh (Tyler No. 4-No. 8, 4.00 mm-2.38 mm). The atomic ratio of Mo:P:Cs:Ba of the resulting catalyst composition (Cat. No. 1) was 12:2:2:1. Similarly Cat. No. 2 to Cat. No. 8 were prepared using 48.5 g of $Bi(NO_3)_3.5H_2O$, 30.8 g of $Cd(NO_3)_2.4H_2O$, 53.8g of $Nb(HC_2O_4)_5$, 26.1 g of $(NH_4)_{10}W_{12}O_{41}.5H_2O$, 12.4 g of $H_3BO_3$, 66.2 g of $Pb(NO_3)_2$ and 17.7 g of $PdCl_2$ instead of $Ba(NO_3)_2$ ii. Cat. No. 9 to Cat. No. 19 were prepared in the same way as mentioned above (i) using 29.5 g of $RbNO_3$ and 20.2 g of $KNO_3$ instead of $CsNO_3$.

(iii). For comparison, Cat. No. (C-1) to Cat. No. (C-11) were prepared in the same way as mentioned above (i) and (ii).

A stainless steel reaction tube 2.5 cm in inside diameter and 60 cm in length was packed with 100 ml. of the catalyst, and heated by a molten metal bath. A feed gas having a methacrolein : $O_2$:$N_2$:$H_2O$ molar ratio of 1:1.5:17.5:10 was passed through the reaction tube while the contact time was adjusted to 1.8 seconds (on the basic of 0°C., and 1 atm.). The results obtained are shown in Table 1.

The reaction temperatures indicated in the table are the maximum temperatures of the catalyst bed at which the best results were obtained.

The results given in Table 1 demonstrate that the catalysts of the present invention give methacrylic acid in high selectivity and high yield in spite of the short contact time. This also shows that the catalysts of the present invention give excellent space time yields of the unsaturated carboxylic acid.

Table 1

$$\text{Conversion (\%)} = \frac{\text{unsaturated aldehyde fed (mol)} - \text{unreacted unsaturated aldehyde (mol)}}{\text{unsaturated aldehyde fed (mol)}} \times 100$$

$$\text{Yield (\%)} = \frac{\text{unsaturated carboxylic acid formed (mol)}}{\text{unsaturated aldehyde fed (mol)}} \times 100$$

$$\text{Selectivity (\%)} = \frac{\text{Yield}}{\text{conversion}} \times 100$$

The abbreviations used in the tables appearing in the Examples have the following meanings.

Cat. = catalyst
RT = reaction temperature
AL = acrolein
MAL = methacrolein
AA = acrylic acid
MAA = methacrylic acid
conv. = conversion
sel. = selectivity Furthermore, in the following examples the indication of the composition of the catalyst does not specifically refer to the presence of oxygen.

EXAMPLE 1 i. 212 g of ammonium molybdate were dissolved in 300 ml. of water with heating, and an aqueous solution of 26.1 g of barium nitrate [$Ba(NO_3)_2$] dissolved in 200 ml. of warm water was added to the solution. The mixture was stirred, and an aqueous solution of 23 g of 85 wt.% phosphoric acid in 50 ml. of water and an aqueous solution obtained by dissolving 39.0 g of cesium nitrate ($CsNO_3$) in 200 ml. of water with heating were further added. Then, the entire mixture was evaporated to dryness with stirring. The solid obtained was cal-

| Run No. | Cat. No. | Catalyst composition (atomic ratio) | RT (°C) | MAL conv. (%) | MAA Yield (%) | (Sel.) |
|---|---|---|---|---|---|---|
| | | This invention | | | | |
| 1-1 | 1 | $Mo_{12} P_2 Cs_2 Ba_1$ | 395 | 74.6 | 49.3 | (66.1) |
| -2 | 2 | $Mo_{12} P_2 Cs_2 Bi_1$ | 422 | 65.2 | 43.4 | (66.4) |
| -3 | 3 | $Mo_{12} P_2 Cs_2 Cd_1$ | 421 | 65.6 | 47.1 | (71.8) |
| -4 | 4 | $Mo_{12} P_2 Cs_2 Nb_1$ | 408 | 64.4 | 43.6 | (67.7) |
| -5 | 5 | $Mo_{12} P_2 Cs_2 W_1$ | 439 | 67.0 | 45.8 | (68.4) |
| -6 | 6 | $Mo_{12} P_2 Cs_2 B_2$ | 428 | 62.7 | 45.3 | (72.2) |
| -7 | 7 | $Mo_{12} P_2 Cs_2 Pb_2$ | 408 | 56.5 | 43.1 | (76.3) |
| -8 | 8 | $Mo_{12} P_2 Cs_2 Pd_1$ | 395 | 73.7 | 48.1 | (65.3) |
| -9 | 9 | $Mo_{12} P_2 K_2 Ba_1$ | 412 | 69.0 | 42.5 | (61.6) |
| -10 | 10 | $Mo_{12} P_2 K_2 Bi_1$ | 425 | 63.1 | 42.0 | (66.0) |
| -11 | 11 | $Mo_{12} P_2 K_2 Cd_1$ | 415 | 60.0 | 40.0 | (67.0) |
| -12 | 12 | $Mo_{12} P_2 K_2 B_2$ | 432 | 51.8 | 38.5 | (74.3) |
| -13 | 13 | $Mo_{12} P_2 Rb_2 Ba_1$ | 404 | 65.4 | 44.3 | (67.7) |
| -14 | 14 | $Mo_{12} P_2 Rb_2 Cd_1$ | 417 | 61.0 | 41.8 | (68.5) |
| -15 | 15 | $Mo_{12} P_2 Rb_2 Nb_1$ | 410 | 60.4 | 40.5 | (67.1) |
| -16 | 16 | $Mo_{12} P_2 Rb_2 W_1$ | 437 | 61.1 | 41.8 | (68.4) |
| -17 | 17 | $Mo_{12} P_2 Rb_2 B_2$ | 430 | 56.3 | 40.0 | (71.0) |
| -18 | 18 | $Mo_{12} P_2 Rb_{1/2} Pb_2$ | 400 | 59.8 | 42.8 | (71.6) |
| -19 | 19 | $Mo_{12} P_2 Rb_2 Pd_1$ | 400 | 70.2 | 44.0 | (62.7) |
| | | Comparison | | | | |
| -20 | (c-1) | $Mo_{12} P_2 Cs_2$ | 409 | 47.1 | 28.3 | (60.1) |
| -21 | (c-2) | $Mo_{12} P_2 K_2$ | 419 | 42.1 | 19.1 | (45.4) |
| -22 | (c-3) | $Mo_{12} P_2 Rb_2$ | 416 | 44.6 | 25.3 | (56.7) |
| -23 | (c-4) | $Mo_{12} P_2 Ba_1$ | 421 | 52.1 | 16.4 | (31.5) |
| -24 | (c-5) | $Mo_{12} P_2 Bi_1$ | 455 | 28.8 | 16.2 | (56.3) |
| -25 | (c-6) | $Mo_{12} P_2 Cd_1$ | 413 | 41.8 | 14.3 | (34.2) |
| -26 | (c-7) | $Mo_{12} P_2 Nb_1$ | 426 | 62.1 | 31.2 | (50.2) |
| -27 | (c-8) | $Mo_{12} P_2 W_1$ | 451 | 20.6 | 12.3 | (59.8) |
| -28 | (c-9) | $Mo_{12} P_2 B_2$ | 428 | 42.1 | 14.2 | (33.7) |
| -29 | (c-10) | $Mo_{12} P_2 Pb_2$ | 433 | 48.1 | 16.0 | (33.3) |

Table 1-continued

| Run No. | Cat. No. | Catalyst composition (atomic ratio) | RT (°C) | MAL conv. (%) | MAA Yield (Sel.) (%) |
|---|---|---|---|---|---|
| -30 (c-11) | | $Mo_{12} P_2 Pd_1$ | 412 | 41.3 | 21.1 (51.1) |

EXAMPLE 2

The procedure of Example 1 was repeated to prepare catalysts shown in Table 2, and the same reaction as in Example 1 was performed. The results obtained are shown in Table 2.

Table 2

| Run No. | Cat. No. | Catalyst composition (atomic ratio) | RT (°C) | MAL conv. (%) | MAA Yield (Sel.) (%) |
|---|---|---|---|---|---|
| II-1 | 20 | $Mo_{12} P_2 Cs_2 Ba_2$ | 404 | 59.7 | 41.1 (68.9) |
| -2 | 21 | $Mo_{12} P_2 Cs_1 Ba_1$ | 400 | 68.5 | 42.0 (61.3) |
| -3 | 22 | $Mo_{12} P_1 Cs_2 Ba_2$ | 400 | 71.3 | 45.4 (63.7) |
| -4 | 23 | $Mo_{12} P_3 Cs_{0.5} Ba_{0.5}$ | 385 | 56.0 | 41.8 (74.6) |
| -5 | 24 | $Mo_{12} P_2 Cs_2 Bi_{0.5}$ | 418 | 64.1 | 38.7 (60.4) |
| -6 | 25 | $Mo_{12} P_2 Cs_1 Bi_1$ | 411 | 65.3 | 36.6 (56.1) |
| -7 | 26 | $Mo_{12} P_2 Cs_1 Nb_1$ | 403 | 67.2 | 44.8 (66.7) |
| -8 | 27 | $Mo_{12} P_2 Cs_2 B_{0.5}$ | 416 | 63.1 | 44.3 (70.2) |
| -9 | 28 | $Mo_{12} P_2 Cs_1 B_2$ | 415 | 57.9 | 38.3 (66.2) |
| -10 | 29 | $Mo_{12} P_2 Cs_2 Pb_1$ | 398 | 53.2 | 37.5 (70.5) |
| -11 | 30 | $Mo_{12} P_1 Cs_2 Pb_1$ | 410 | 61.0 | 39.3 (64.4) |
| -12 | 31 | $Mo_{12} P_2 K_1 Ba_1$ | 405 | 65.4 | 41.0 (62.7) |
| -13 | 32 | $Mo_{12} P_2 K_{0.5} Cd_1$ | 410 | 62.3 | 39.8 (63.9) |
| -14 | 33 | $Mo_{12} P_1 K_1 W_1$ | 405 | 68.3 | 46.3 (67.8) |
| -15 | 34 | $Mo_{12} P_2 K_1 B_4$ | 425 | 59.9 | 40.0 (66.8) |
| -16 | 35 | $Mo_{12} P_2 Rb_1 Ba_1$ | 402 | 65.0 | 43.8 (67.4) |
| -17 | 36 | $Mo_{12} P_1 Rb_{0.5} W_{0.5}$ | 379 | 64.8 | 42.2 (65.1) |
| -18 | 37 | $Mo_{12} P_1 Rb_1 Pd_1$ | 400 | 63.8 | 41.0 (64.3) |
| -19 | 38 | $Mo_{12} P_2 Rb_1 Cs_1 Bi_1$ | 425 | 64.0 | 41.5 (64.8) |
| -20 | 39 | $Mo_{12} P_2 Rb_1 Cs_1 Cd_1$ | 419 | 63.3 | 45.8 (72.4) |
| -21 | 40 | $Mo_{12} P_2 Rb_2 Ba_{0.5} Cd_{0.5}$ | 410 | 64.1 | 43.8 (68.3) |
| -22 | 41 | $Mo_{12} P_2 Cs_2 Bi_{0.5} Nb_{0.5}$ | 405 | 75.0 | 48.8 (65.1) |
| -23 | 42 | $Mo_{12} P_2 Cs_2 Bi_{0.5} W_{0.5}$ | 411 | 73.2 | 51.0 (69.7) |
| -24 | 43 | $Mo_{12} P_2 Cs_1 K_1 Pb_2$ | 395 | 56.3 | 40.9 (72.6) |
| -25 | 44 | $Mo_{12} P_2 Cs_2 B_1 Pb_1$ | 421 | 57.3 | 41.1 (71.1) |

EXAMPLE 3

Acrolein was oxidized under the same conditions as in Example 1 using each of the catalysts shown in Table 3 which were obtained in Examples 1 and 2, while adjusting the composition of the feed gas to acrolein: $O_2:N_2:H_2O = 1:2:8:9$ (molar ratio). The results are shown in Table 3.

Table 3

| Run No. | Cat. No. | Catalyst composition (atomic ratio) | RT °C | AL Conv. (%) | AA Yield (Sel) % |
|---|---|---|---|---|---|
| III-1 | 1 | $Mo_{12} P_2 Cs_2 Ba_1$ | 425 | 85.4 | 73.4 (85.9) |
| -2 | 2 | $Mo_{12} P_2 Cs_2 Bi_1$ | 448 | 68.8 | 60.0 (87.2) |
| -3 | 7 | $Mo_{12} P_2 Cs_2 Pb_2$ | 401 | 80.0 | 70.7 (88.4) |
| -4 | 12 | $Mo_{12} P_2 K_2 B_2$ | 415 | 75.1 | 72.1 (96.0) |

EXAMPLE 4

Methacrolein was oxidized continuously for prolonged periods of time under the same conditions in Example 1 using each of the catalysts shown in Table 4 which were obtained in Examples 1 and 2. The performance of each catalyst used after a lapse of 30 days of reaction is shown in Table 5. The temperature of the molten metal bath was kept almost constant during the reaction. In the table, "0" under "time that elapsed" means the initial stage of the reaction. It is seen from Table 5 that the catalysts prepared according to the present invention do not lose their activity even after a lapse of a long period of time, and prove to be excellent catalysts having a very long active lifetime. On the other hand, the activity of the comparison catalysts decreases abruptly within a short period of time, and therefore, they have a short active lifetime.

Table 4

| Run No. | Cat. No. | Catalyst composition (atomic ratio) | Time that elapsed (days) | RT (°C) | MAL conv. (%) | MAA Yield (Sel.) (%) |
|---|---|---|---|---|---|---|
| | | This invention | | | | |
| IV-1 | 1 | $Mo_{12} P_2 Cs_2 Ba_1$ | 0* | 395 | 74.6 | 49.3 (66.1) |
| | | | 30 | 394 | 75.0 | 49.0 (65.3) |
| -2 | 3 | $Mo_{12} P_2 Cs_2 Cd_1$ | 0 | 421 | 65.6 | 47.1 (71.8) |
| | | | 30 | 420 | 65.1 | 48.5 (74.5) |
| -3 | 4 | $Mo_{12} P_2 Cs_2 Nb_1$ | 0 | 408 | 64.4 | 43.6 (67.7) |
| | | | 30 | 411 | 64.0 | 43.5 (68.0) |
| -4 | 6 | $Mo_{12} P_2 Cs_2 B_2$ | 0 | 428 | 62.7 | 45.3 (72.2) |
| | | | 30 | 426 | 62.5 | 45.1 (72.2) |
| -5 | 7 | $Mo_{12} P_2 Cs_2 Pb_2$ | 0 | 408 | 56.5 | 43.1 (76.3) |
| | | | 30 | 401 | 55.7 | 42.2 (75.8) |

Table 4-continued

| Run No. | Cat. No. | Catalyst composition (atomic ratio) | Time that elapsed (days) | RT (°C) | MAL conv. (%) | MAA Yield (Sel.) (%) |
|---|---|---|---|---|---|---|
| -6 | 10 | $Mo_{12} P_2 K_2 Bi_1$ | 0 | 425 | 63.1 | 42.0 (66.0) |
| | | | 30 | 421 | 61.8 | 43.1 (69.7) |
| -7 | 12 | $Mo_{12} P_2 K_2 B_2$ | 0 | 432 | 51.8 | 38.5 (74.3) |
| | | | 30 | 425 | 50.9 | 39.0 (76.6) |
| -8 | 13 | $Mo_{12} P_2 Rb_2 Ba_1$ | 0 | 404 | 65.4 | 44.3 (67.7) |
| | | | 30 | 404 | 67.0 | 44.4 (66.3) |
| -9 | 16 | $Mo_{12} P_2 Rb_2 W_1$ | 0 | 437 | 61.1 | 41.8 (68.4) |
| | | | 30 | 437 | 61.0 | 41.7 (68.4) |
| -10 | 17 | $Mo_{12} P_2 Rb_2 B_2$ | 0 | 430 | 56.3 | 40.0 (71.0) |
| | | | 30 | 430 | 56.2 | 40.0 (71.2) |
| -11 | 39 | $Mo_{12} P_2 Rb_1 Cs_1 Cd_1$ | 0 | 419 | 63.3 | 45.8 (72.4) |
| | | | 30 | 420 | 64.2 | 46.5 (72.4) |
| -12 | 41 | $Mo_{12} P_2 Cs_2 Bi_{0.5} Nb_{0.5}$ | 0 | 405 | 75.0 | 48.8 (65.1) |
| | | | 30 | 405 | 75.1 | 48.8 (65.0) |
| -13 | 42 | $Mo_{12} P_2 Cs_2 Bi_{0.5} W_{0.5}$ | 0 | 411 | 73.2 | 51.0 (69.7) |
| | | | 30 | 406 | 72.8 | 53.8 (73.9) |
| | | Comparison | | | | |
| -14 | (c-1) | $Mo_{12} P_2 Cs_2$ | 0 | 409 | 47.1 | 28.3 (60.1) |
| | | | 30 | 386 | 38.2 | 19.5 (51.9) |
| -15 | (c-2) | $Mo_{12} P_2 K_2$ | 0 | 419 | 42.1 | 19.1 (45.4) |
| | | | 30 | 390 | 31.4 | 10.0 (31.8) |
| -16 | (c-3) | $Mo_{12} P_2 Rb_2$ | 0 | 416 | 44.6 | 25.3 (56.7) |
| | | | 30 | 410 | 32.6 | 15.9 (48.8) |
| -17 | (c-4) | $Mo_{12} P_2 Ba_1$ | 0 | 421 | 52.1 | 16.4 (31.5) |
| | | | 6 | 421 | 52.0 | 16.3 (31.3) |
| -18 | (c-5) | $Mo_{12} P_2 Bi_1$ | 0 | 455 | 28.8 | 16.2 (56.3) |
| | | | 6 | 453 | 27.1 | 10.9 (40.2) |
| -19 | (c-6) | $Mo_{12} P_2 Cd_1$ | 0 | 413 | 41.8 | 14.3 (34.2) |
| | | | 6 | 412 | 41.5 | 14.4 (34.7) |
| -20 | (c-7) | $Mo_{12} F_2 Nb_1$ | 0 | 426 | 62.1 | 31.2 (50.2) |
| | | | 6 | 430 | 59.6 | 20.1 (33.7) |
| -21 | (c-8) | $Mo_{12} P_2 W_1$ | 0 | 451 | 20.6 | 12.3 (59.8) |
| | | | 6 | 450 | 19.3 | 11.4 (59.1) |
| -22 | (c-9) | $Mo_{12} P_2 B_2$ | 0 | 428 | 42.1 | 14.2 (33.7) |
| | | | 6 | 421 | 40.4 | 13.6 (33.7) |
| -23 | (c-10) | $Mo_{12} P_2 Pb_2$ | 0 | 433 | 48.1 | 16.0 (33.3) |
| | | | 6 | 415 | 40.7 | 13.3 (32.7) |
| -24 | (c-11) | $Mo_{12} P_2 Bi_{0.5} Nb_{0.5}$ | 0 | 365 | 78.3 | 45.7 (58.5) |
| | | | 13 | 324 | 55.3 | 17.3 (31.3) |
| -25 | (c-12) | $Mo_{12} P_2 Bi_{0.5} W_{0.5}$ | 0 | 368 | 81.6 | 50.0 (61.3) |
| | | | 13 | 322 | 60.0 | 18.1 (30.2) |

What we claim is:

1. A process for the preparation of an unsaturated carboxylic acid which comprises reacting an unsaturated aldehyde selected from acrolein and methacrolein with molecular oxygen in the vapor phase in the presence of an oxidation catalyst composition consisting essentially of a catalytic oxide of molybdenum, phosphorus, at least one element selected from the group consisting of rubidium, cesium and potassium, and at least one element selected from the group consisting of barium, cadmium, tungsten, bismuth, niobium, boron, lead and palladium, the catalyst composition having the following empirical formula $$Mo_a P_b L_c T_d O_e$$

wherein L is at least one element selected from the group consisting of Rb, Cs and K; T is at least one element selected from the group consisting of Ba, Cd, W, Bi, Nb, B, Pb and Pd; and $a$, $b$, $c$, $d$ and $e$ each represent the number of atoms of each element: the atomic ratio of $a:b:c:d$ is 12:0.1–8:0.1–8:0.1–8 and $e$ is the number of oxygen atoms determined by the valence requirement of the other elements present.

2. The process of claim 1, wherein the unsaturated aldehyde is acrolein.

3. The process of claim 1, wherein the unsaturated aldehyde is methacrolein.

4. The process of claim 1, wherein the reaction temperature is 300° to 500°C.

5. The process of claim 1, wherein the source of molecular oxygen is air.

6. The process of claim 1, wherein an inert diluent gas is introduced into the reaction zone.

7. The process of claim 1, wherein the catalyst is diluted with an inert diluent or supported on an inert carrier.

8. The process of claim 1, wherein the atomic ratio of $a:b:c:d$ is 12:0.3–5:0.3–5:0.3–5.

9. The process of claim 1, wherein L is Rb.

10. The process of claim 1, wherein L is Cs.

11. The process of claim 1, wherein L is K.

12. The process of claim 1 wherein T is Ba.

13. The process of claim 1 wherein T is Cd.

14. The process of claim 1 wherein T is Pd.

15. The process of claim 1 wherein said catalyst contains both Rb and Cs and T is Cd.

16. The process of claim 1 wherein said catalyst contains Ba and Cd and L is Rb.